(12) United States Patent
Hanebuchi et al.

(10) Patent No.: US 7,316,480 B2
(45) Date of Patent: Jan. 8, 2008

(54) EYE REFRACTIVE POWER MEASUREMENT APPARATUS

(75) Inventors: Masaaki Hanebuchi, Nukata-gun (JP); Mitsuhiro Gono, Toyokawa (JP); Mikio Kurachi, Hazu-gun (JP); Naoki Isogai, Nishio (JP)

(73) Assignee: Nidek Co., Ltd., Gamagori-shi (JP)

( * ) Notice: Subject to any disclaimer, the term of this patent is extended or adjusted under 35 U.S.C. 154(b) by 108 days.

(21) Appl. No.: 10/949,297

(22) Filed: Sep. 27, 2004

(65) Prior Publication Data

US 2005/0068497 A1    Mar. 31, 2005

(30) Foreign Application Priority Data

Sep. 30, 2003    (JP)    ............................. 2003-342618

(51) Int. Cl.
*A61B 3/10*    (2006.01)
(52) U.S. Cl. ...................... 351/211; 351/206; 351/209; 351/212; 351/221
(58) Field of Classification Search ........ 351/205–208, 351/210, 213–215, 221, 209, 211, 212
See application file for complete search history.

(56) References Cited

U.S. PATENT DOCUMENTS

| | | | |
|---|---|---|---|
| 5,463,430 A | 10/1995 | Isogai et al. | |
| 5,523,809 A | 6/1996 | Kohayakawa | |
| 6,002,484 A | 12/1999 | Rozema et al. | |
| 6,079,828 A * | 6/2000 | Fujieda | 351/206 |
| 6,257,722 B1 * | 7/2001 | Toh | 351/208 |
| 6,409,344 B1 | 6/2002 | Hayashi | |

FOREIGN PATENT DOCUMENTS

| | | |
|---|---|---|
| JP | 05-031075 A | 2/1993 |
| JP | 08-103413 A | 4/1996 |
| JP | 11-225963 A | 8/1999 |
| WO | WO 99/66828 A1 | 12/1999 |

* cited by examiner

*Primary Examiner*—Hung Xuan Dang
(74) *Attorney, Agent, or Firm*—Oliff & Berridge, PLC

(57) ABSTRACT

An eye refractive power measurement apparatus which is capable of measuring even an eye with a small pupil diameter and measuring a normal eye with a large enough pupil diameter with accuracy and stability. The apparatus includes a measurement optical system for photo-receiving measurement light from a fundus via a ring-shaped aperture arranged at an approximately conjugate position with a pupil by using a photodetector, a changing device for changing a size of the ring-shaped aperture on a pupillary surface to a size different in both inside diameter and outside diameter, and a calculation device for calculating the eye refractive power based on a photo-receiving result obtained by the photodetector.

8 Claims, 6 Drawing Sheets

EYE REFRACTIVE POWER MEASUREMENT APPARATUS

BACKGROUND OF THE INVENTION

1. Field of the Invention

The present invention relates to an eye refractive power measurement apparatus for measuring eye refractive power of an eye of an examinee objectively.

2. Description of Related Art

Conventionally, there is known an eye refractive power measurement apparatus which projects spot-shaped measurement light onto a fundus via a central pupillary portion and photo-receives reflection light from the fundus via a peripheral pupillary portion and a ring-shaped aperture (opening) which is arranged at an optically conjugate position with a pupil using a two-dimensional photodetector or the like to obtain eye refractive power based on a photo-receiving result thereof (see Japanese Patent Application Unexamined Publication No. Hei11-225963). In such an apparatus, in order to ensure measurement accuracy, the size of the ring-shaped aperture is set so as to photo-receive the reflection light from the fundus via a ring-shaped region of 2 mm in inside diameter and 3 mm in outside diameter on a pupillary surface.

However, some of the aged people and the like have a pupil which is not more than 2 mm in diameter, and there is a case where measurement cannot be performed with a constitution that the measurement light from the fundus is photo-received via the ring-shaped region of 2 mm in inside diameter and 3 mm in outside diameter on the pupillary surface. In order to cope with this problem, it is conceivable that the ring-shaped region on the pupillary surface is made smaller to be 1.4 mm in inside diameter and 2.4 mm in outside diameter (i.e., the size of the ring-shaped aperture is made smaller). However, in this case, corneal reflection or crystalline lens reflection of the projected measurement light tends to become noise, and for a normal eye with a large enough pupil diameter, measurement accuracy is sometimes contrarily lowered.

SUMMARY OF THE INVENTION

An object of the invention is to overcome the problems described above and to provide an eye refractive power measurement apparatus which is capable of measuring even an eye with a small pupil diameter and measuring a normal eye with a large enough pupil diameter with accuracy and stability.

To achieve the objects and in accordance with the purpose of the present invention, an eye refractive power measurement apparatus has a measurement optical system for photo-receiving measurement light from a fundus via a ring-shaped aperture arranged at an approximately conjugate position with a pupil by using a photodetector, a changing device for changing a size of the ring-shaped aperture on a pupillary surface to a size different in both inside diameter and outside diameter, and a calculation device for calculating the eye refractive power based on a photo-receiving result obtained by the photodetector.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
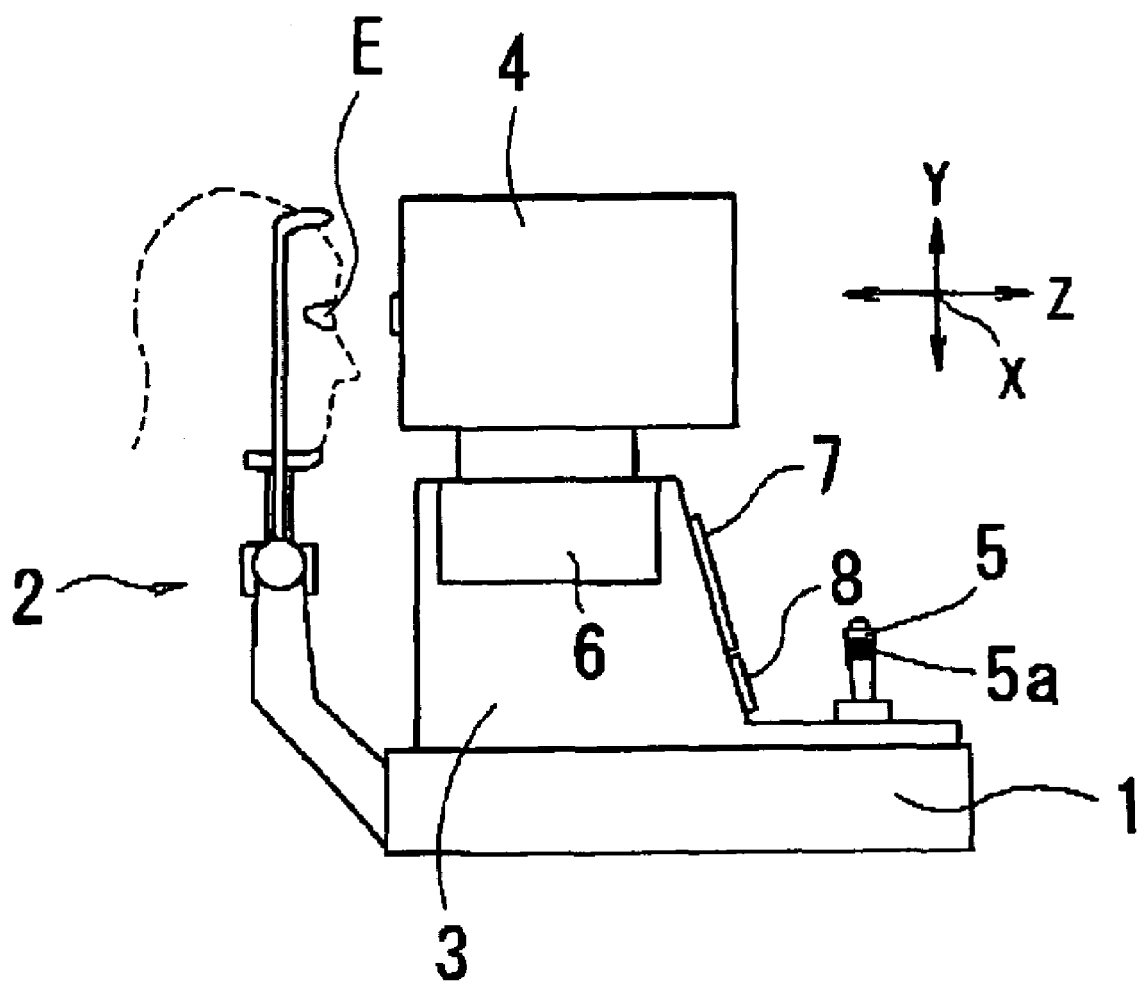
FIG. 1 is a view showing a schematic configuration of an eye refractive power measurement apparatus consistent with one embodiment of the present invention.

A detailed description of one preferred embodiment of an eye refractive power measurement apparatus embodied by the present invention is provided below with reference to the accompanying drawings. FIG. 1 is a view showing a schematic configuration of the eye refractive power measurement apparatus consistent with one embodiment of the present invention. The measurement apparatus is provided with a base 1, a face-supporting unit 2 being attached to the base 1, a mobile base 3 being provided movably on the base 1, and a measurement part 4 being provided movably on the mobile base 3 and storing optical systems described later. The measurement part 4 is moved in a right/left direction (an X-direction), an up/down direction (a Y-direction), and a back/forth direction (a Z-direction) with respect to an eye E of an examinee by an X-, Y- and Z-movement part 6 provided to the mobile base 3. The movement part 6 is constituted of a sliding mechanism, a motor, and the like which are provided for each of the X-, Y- and Z-directions. Further, the mobile base 3 is moved in the X- and Z-directions on the base 1 through tilting operation of a joystick 5. And, the measurement part 4 is moved in the Y-direction on the mobile base 3 through rotating operation of a rotation knob 5a. Arranged on the mobile base 3 are a monitor 7 for displaying various information such as an observation image and a measurement result of the eye E, and a switch part 8 provided with switches (keys) for performing various settings.

Figure 2:
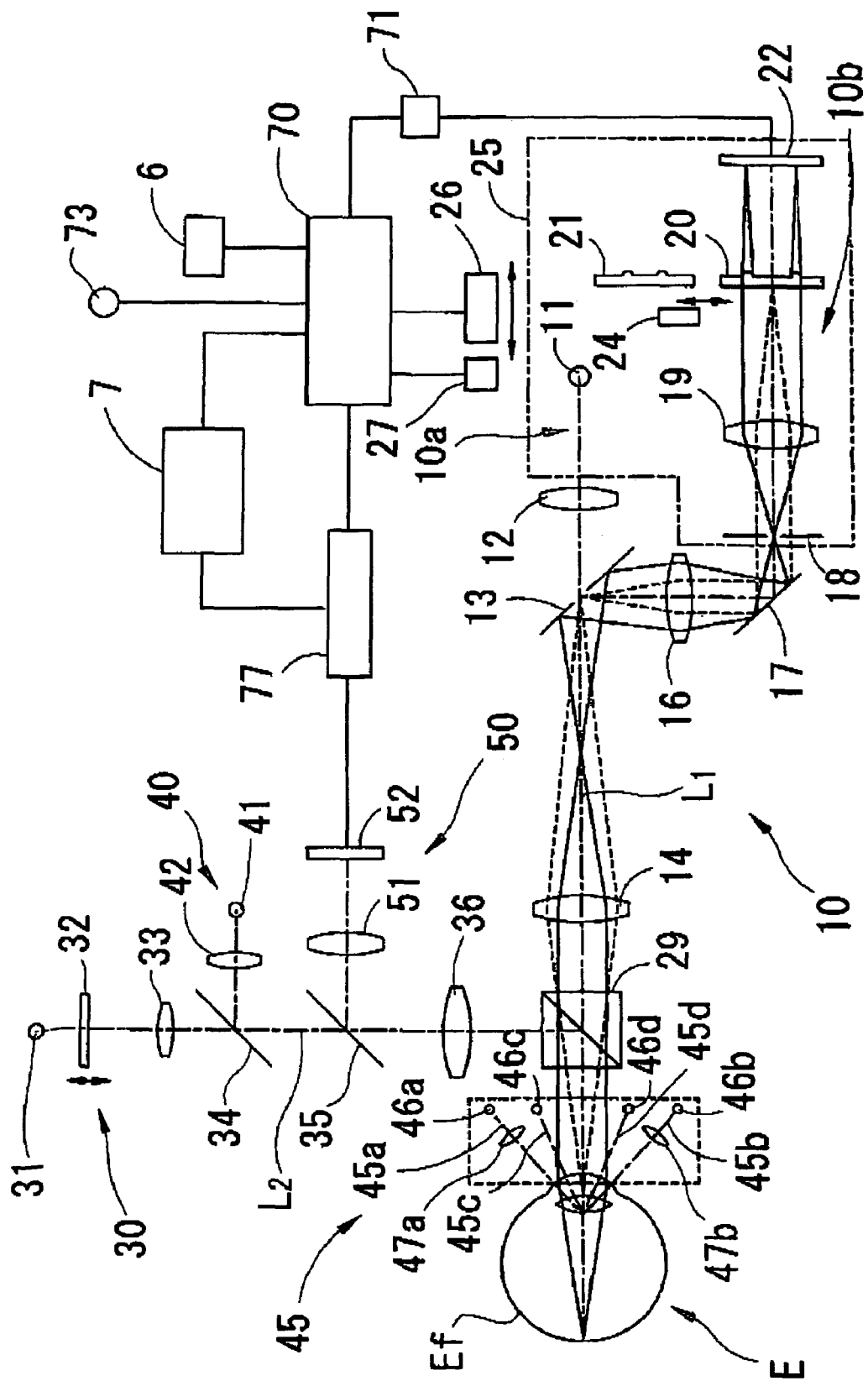
FIG. 2 is a view showing a schematic configuration of optical systems and a control system in the eye refractive power measurement apparatus.

FIG. 2 is a view showing a schematic configuration of optical systems and a control system in the measurement apparatus. A measurement optical system 10 is constituted of a projection optical system 10a for projecting spot-shaped measurement light onto a fundus Ef via a central pupillary portion of the eye E, and a photo-receiving optical system 10b for photo-receiving reflection light from the fundus Ef via a peripheral pupillary portion. The projection optical system 10a includes an infrared point light source 11 such as an LED and an SLD, a relay lens 12, a hole mirror 13, and an objective lens 14 for measurement which are arranged on a measurement optical axis L1. The light source 11 is arranged to have a positional relationship optically approximately conjugate with the fundus Ef. Disposed between the lens 14 and the eye E is a dichroic mirror (or a half mirror) 29, having a property of reflecting visible light and near infrared light and transmitting infrared light, which reflects reflection light from an anterior-segment of the eye E toward an observation optical system 50 and directs fixation target light from a fixation target presenting optical system 30 and alignment target light from an alignment target projection optical system 40 toward the eye E.

The photo-receiving optical system 10b shares the lens 14 and the mirror 13 in the projection optical system 10a and includes a relay lens 16 and a reflection mirror 17 which are arranged on the optical axis L1 in a reflecting direction of the mirror 13, and a photo-receiving diaphragm 18, a collimator lens 19 and an image-pickup element 22 being a two-dimensional photodetector such as a CCD which are arranged on the optical axis L1 in a reflecting direction of the mirror 17. In addition, the photo-receiving optical system 10b further includes ring lenses 20 and 21, and switching is made to arrange one of them on the optical axis L1 between the lens 19 and the image-pickup element 22. The switching between the ring lens 20 and the ring lens 21 is performed by a movement part 24. The diaphragm 18 and the image-pickup element 22 are arranged to have a positional relationship optically approximately conjugate with the fundus Ef. An output of the image-pickup element 22 is inputted to a control part 70 via an image processing part 71.

Figure 3A:
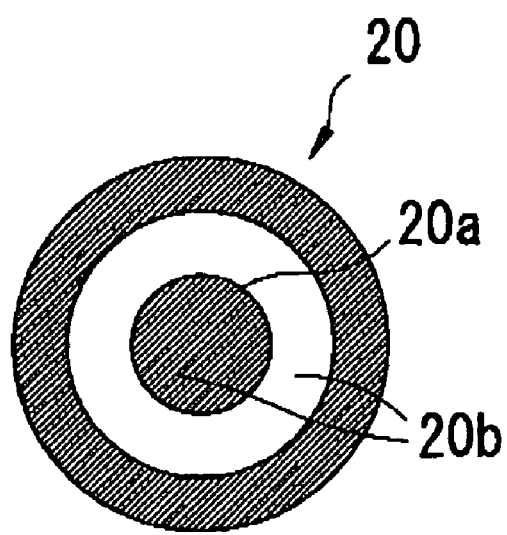
FIGS. 3A and 3B are views showing a schematic configuration of a ring lens.
Figure 3B:
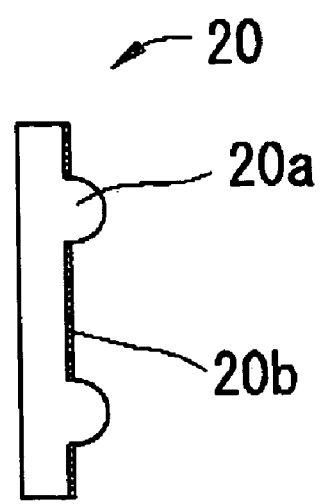

As shown in FIGS. 3A and 3B, the ring lens 20 is constituted of a lens portion 20a where a cylindrical lens is formed in a ring shape on one side of a transparent plate, and a light shielding portion 20b formed by coating for light shielding which is provided to other portions than the ring-shaped cylindrical lens of the lens-portion 20a, owing to such constitution, a ring-shaped aperture (opening) is formed on the ring lens 20. Incidentally, in the ring lens 20, the ring-shaped aperture (the light shielding portion 20b) is arranged to have a positional relationship optically approximately conjugate with a pupil of the eye E (which is not necessarily strictly conjugate but may be conjugate with needed accuracy in relation to measurement accuracy). Therefore, the reflection light from the fundus Ef passes through the peripheral pupillary portion and is picked up in a ring shape of a size corresponding to the formed ring-shaped aperture. When parallel light enters the ring lens 20, a ring image of the same size as the ring-shaped aperture is formed on the image-pickup element 22 arranged at a focal point of the ring lens 20. Besides, the ring lens 20 may be constituted of separate members as the ring portion 20a and the light shielding portion 20b. And, the ring lens 21 has the same constitution as the ring lens 20.

The ring lens 20 and the ring lens 21 have the ring-shaped apertures which are different in both the inside diameter and the outside diameter. The ring lens 20 is used for an eye with a large pupil diameter, and the size of its ring-shaped aperture (referred to simply as a ring size, hereinafter) is for example 2.0 mm in inside diameter and 2.8 mm in outside diameter on the pupillary surface. In contrast, the ring lens 21 is used for an eye with a small pupil diameter, and the size of its ring-shaped aperture (the ring size) is for example 1.4 mm in inside diameter and 2.4 mm in outside diameter on the pupillary surface.

Additionally, the light source 11 in the projection optical system 10a together with the diaphragm 18, the lens 19, the ring lenses 20 and 21, and the image-pickup element 22 in the photo-receiving optical system 10b are arranged movable in the optical axis L1 direction integrally as a movable unit 25. The movable unit 25 is moved in the optical axis L1 direction by a movement part 26, and is moved in accordance with a spherical refractive error (spherical refractive power) of the eye E, so that the spherical refractive error is corrected and the light source 11, the diaphragm 18, and the image-pickup element 22 are brought to have a positional relationship optically approximately conjugate with the fundus Ef. A travel position of the movable unit 25 is detected by a potentiometer 27. Besides, the mirror 13 and the ring lenses 20 and 21 are arranged to have a positional relationship optically approximately conjugate with the pupil of the eye E under a fixed magnification regardless of a travel amount of the movable unit 25.

The fixation target presenting optical system 30 includes a visible light source 31, a fixation target 32, a projection lens 33, a dichroic mirror 34 having a property of reflecting near infrared light and transmitting visible light, a half mirror 35, and an objective lens 36 for observation which are arranged on an optical axis L2 which is made coaxial with the optical axis L1 by the mirror 29. The light source 31 and the fixation target 32 are moved in the optical axis L2 direction to fog the eye E. The fixation target light through illumination of the fixation target 32 by the light source 31 is projected onto the eye E through the lens 33 to the mirror 29. The eye E can thereby perform fixation.

The alignment target-projection optical system 40, for projecting an alignment target for detection of an alignment state in the X- and Y-directions onto the eye E from the front, shares the mirror 34 to the lens 36 in the fixation target presenting optical system 30 and includes a near infrared point light source 41 such as an LED and an SLD, and a condenser lens 42 which are arranged on the optical axis L2 in a reflecting direction of the mirror 34. The alignment target light from the light source 41 is made approximately parallel light and projected onto the eye E.

An alignment target projection optical system 45, for projecting alignment targets for detection of an alignment state in the Z-direction onto the eye E obliquely, includes a pair of first projection optical systems 45a and 45b having optical axes which are arranged symmetrically with respect to the optical axis L1, and a pair of second projection optical systems 45c and 45d having optical axes which are arranged symmetrically with respect to the optical axis L1 and form a smaller angle than the first projection optical systems 45a and 45b. The first projection optical systems 45a and 45b have near infrared point light sources 46a and 46b, and collimator lenses 47a and 47b, and project alignment targets at an infinite distance onto the eye E with approximately parallel light. In contrasts the second projection optical systems 45c and 45d have near infrared point light sources 46c and 46d and project alignment targets at a finite distance onto the eye E with divergent light.

The observation optical system 50 shares the lens 36 and the mirror 35, and includes an image-pickup lens 51 and an image-pickup element 52 such as a CCD which are arranged on the optical axis L2 in a reflecting direction of the mirror 35. An output of the image-pickup element 52 is inputted to the monitor 7 via an image processing part 77. An image of the anterior-segment of the eye E through an unillustrated near infrared light source for anterior-segment illumination is formed on an image-pickup surface of the image-pickup element 52 through the mirror 29 to the lens 51 to be displayed on the monitor 7 as an observation image. Incidentally, the observation optical system 50 doubles as an optical system for detecting each alignment target image formed on a cornea of the eye E and an optical system for detecting the pupil of the eye E, and positions of the alignment target images, a position of the pupil and the like are detected by the image processing part 77. The control part 70 detects an applicability of the alignment state and a state of the pupil of the eye E based on a signal from the image processing part 77.

Here will be described operation of the apparatus with the aforementioned constitution. First, a face of the examinee is fixed to the face-supporting unit 2, and then the alignment targets are projected onto the cornea of the eye E for aligning the measurement part 4 with the eye E. The alignment state in the X- and Y-directions of the measurement part 4 with the eye E is detected from a positional relationship between the alignment target image formed by the alignment target projection optical system 40 and the optical axis L1 (L2), and the alignment state in the Z-direction is detected from a positional relationship between four alignment target images formed by the alignment target projection optical system 45. The applicability of the alignment state in the Z-direction is detected through a comparison of a distance between two target images at an infinite distance by the first projection optical systems 45a and 45b to a distance between two target images at a finite distance by the second projection optical systems 45c and 45d. As for the targets at an infinite distance, even if the Z-direction is changed, the distance therebetween scarcely changes. Contrarily, as for the targets at a finite distance, the distance therebetween changes in accordance with the change in the Z-direction. By utilizing this property, the alignment state in the Z-direction can be determined (see U.S. Pat. No. 5,463,430 corresponding to Japanese Patent Application Unexamined publication No. Hei6-46999).

The control part 70 moves the measurement part 4 in the X- and Y-directions based on the alignment target image formed by the alignment target projection optical system 40, and moves the measurement part 4 in the Z-direction based on the four alignment target images formed by the alignment target projection optical system 45. When the alignment state in each of the X-, Y- and Z-directions falls within their respective predetermined permissible ranges, the control part 70 judges alignment completion and automatically generates (inputs) a measurement starting signal to implement measurement. In the case of manual measurement, an examiner operates the joystick 5 and the like to complete alignment, and then pushes a measurement starting switch 73 to input the measurement starting signal and implement measurement.

The control part 70 lights the light source 11 based on the input of the measurement starting signal and drives and controls the movement part 24 to arrange the ring lens 20 on the optical axis L1. The measurement light from the light source 11 is projected onto the fundus Ef through the lens 12 to the mirror 29 to form a point-light-source image in a spot shape on the fundus Ef. Light of the point-light-source image formed on the fundus Ef is reflected and scattered to be ejected from the eye E, and is collected by the lens 14 and collected again on an aperture (opening) surface of the diaphragm 18 through the mirror 13 to the mirror 17. Then, the light is made approximately parallel light by the lens 19 and is made ring-shaped light by the ring lens 20 to be photo-received on the image-pickup element 22. Besides, a state where the ring lens 20 of a large ring size is arranged on the optical axis L1 is set as the initial state. In the projection optical system 10a, thin measurement light is projected onto the fundus Ef via the central pupillary portion of the eye E, and in the photo-receiving optical system 10b, the reflection light from the fundus Ef is photo-received (picked up) via the peripheral pupillary portion. When the ring lens 20 is arranged on the optical axis L1, the ring-shaped light of 2.0 mm in inside diameter and 2.8 mm in outside diameter on the pupillary surface is photo-received (picked up).

Here, if the eye E is emmetropia, the image-pickup element 22 and the fundus Ef become approximately conjugate, and the reflection light from the fundus Ef enters the ring lens 20 as parallel light; therefore, a ring image of the same size and shape as the ring-shaped aperture of the ring lens 20 is formed on the image-pickup element 22. On the other hand, in a case where the eye E has abnormality in a spherical refractive component, a ring image of the size corresponding to an error of the spherical refractive component is formed on the image-pickup element 22. Further, in a case where the eye E has abnormality in an astigmatic refractive component, an oval ring image corresponding to an error of the astigmatic refractive component is formed on the image-pickup element 22. Accordingly, by analyzing the size and shape of the ring image formed on the image-pickup element 22, a refractive error in each meridian direction can be obtained, and by providing predetermined processing thereto, values S (spherical power), C (astigmatic (cylindrical) power) and A (an astigmatic axial angle) can be obtained. Besides, the size and shape of the ring image can be obtained from an edge position of the ring image, the barycenter or a peak position of light intensity level of the ring image, and the like. For the normal eye with a large enough pupil diameter, the use of the ring lens 20 of a larger ring size enables measurement while maintaining measurement accuracy.

Further, the light source 11, the diaphragm 18, the lens 19, the ring lens 20, and the image-pickup element 22 as the movable unit 25 are integrally moved in the optical axis L1 direction to make the ring image on the image-pickup element 22 become thinnest or brightest, or to make an average size of the ring image become the same as the ring size of the ring lens 20, 80 that the light source 11, the diaphragm 18, and the image-pickup element 22 have a positional relationship approximately conjugate with the fundus Ef. Then, the travel position of the movable unit 25 detected by the potentiometer 27 is converted to the error of the spherical refractive component. The refractive error in each meridian direction of the eye E can be obtained as the sum of this error of the spherical refractive component and the refractive error in each meridian direction obtained by the ring image on the image-pickup element 22. With such constitution that the movable unit 25 is moved in the optical axis L1 direction as mentioned above, measurement of a great refractive error can be supported while not scaling down resolution upon ring image analysis and not enlarging the size of a photo-receiving surface of the image-pickup element 22.

In such refractive power measurement, in a case where the eye with a small pupil diameter is measured, the reflection light from the fundus Ef to be picked up by the ring lens 20 is repelled by an iris, and the ring image becomes not formed on the image-pickup element 22. Therefore, with the ring lens 20 alone, the measurement accuracy is lowered or the measurement itself cannot be performed. In such a case, the ring lens 21 is used. In a case where the ring image detected by the image-pickup element 22 has a crack or intensity is not more than a fixed level, the control part 70 judges that the reflection light from the fundus Ef to be picked up by the ring lens 20 is being repelled by the iris, and drives and controls the movement part 24 to perform switching to arrange the ring lens 21 of a smaller ring size on the optical axis L1 when the ring lens 21 is arranged on the optical axis L1, ring-shaped light of 1.4 mm in inside diameter and 2.4 mm in outside diameter on the pupillary surface is photo-received (picked up). And, by analyzing the size and shape of the ring image formed on the image-pickup element 22 in the same manner as mentioned above, the refractive values can be obtained. The measurement can be thereby performed even to the eye with a small pupil diameter.

Incidentally, a pupil diameter, an eccentricity state of a pupil position (a deviation state of a pupil center from the optical axis L1, or the like) at the time of the alignment completion and the like may be detected from the image of the anterior-segment of the eye E picked up by the image-pickup element 52 in the observation optical system 50 to judge whether or not it is necessary to switch the ring lens 20 to the ring lens 21. Additionally, this switching is controlled by the control part 70, and alternatively, the examiner may determine to perform switching through switch operation while observing the pupil diameter, the pupil position and the like displayed on the monitor 7.

Besides, in the aforementioned measurement, based on a photo-receiving result of the ring image, the fixation target 32 is once brought to have a positional relationship approximately conjugate with the fundus Ef, and then the fixation target 32 is moved so as to perform fogging by an adequate amount of diopter, and main measurement is performed in a state where the eye E is fogged.

Further, in the above embodiment, two ring lenses such as the ring lenses 20 and 21 are used which have the ring-shaped apertures of different sizes; however, more lenses of a variety of ring sizes may be used.

In addition, the constitution for picking up the ring-shaped light from the peripheral pupillary portion of the eye E includes a constitution, as mentioned in Japanese Patent Application unexamined Publication No. Hei5-31075, where a ring-shaped aperture member (diaphragm) having six apertures (openings) on one concentric circle in at least three meridian directions is arranged at an optically approximately conjugate position with the pupil. In this case, instead of the ring lenses, wedge prisms and photo-receiving lenses corresponding to the six, apertures of the ring-shaped aperture member are arranged, so that six separate ring images can be formed on the image-pickup element 22. And, a plurality of the ring-shaped aperture member with six apertures and the wedge prisms in different sizes may be prepared and switched.

Further, the ring lens 20 and the ring lens 21 may be constituted to be sequentially switched based on the measurement starting signal (after the input). In this constitution, image capture of one frame at the image-pickup element 22 is synchronized to the switching, and each ring image is detected and processed by the image processing part 71. In a case where the eye with a small pupil diameter is measured, as mentioned above, the ring image by the ring lens 20 becomes not formed on the image-pickup element 22. In this case, by obtaining the refractive values based on the ring image by the ring lens 21, measurement to suit the eye with a small pupil diameter can be performed. In contrast, when the ring image by the ring lens 20 is formed on the image-pickup element 22, the refractive values are obtained based on this ring image. Alternatively, when each ring image by the ring lenses 20 and 21 bears no problem, the refractive values may be obtained from an average of the refractive errors obtained from both the ring images.

Thereby, for the normal eye with a large enough pupil diameter, measurement can be performed while maintaining measurement accuracy.

Further, if the aforementioned constitution is employed where the ring lenses 20 and 21 of different ring sizes are switched and arranged and each ring image is detected and processed in synchronization with the switching, there exists no situation in which a plurality of the ring images are detected and processed while they are overlapped with each other; therefore, an accurate measurement result can be obtained.

Figure 4:
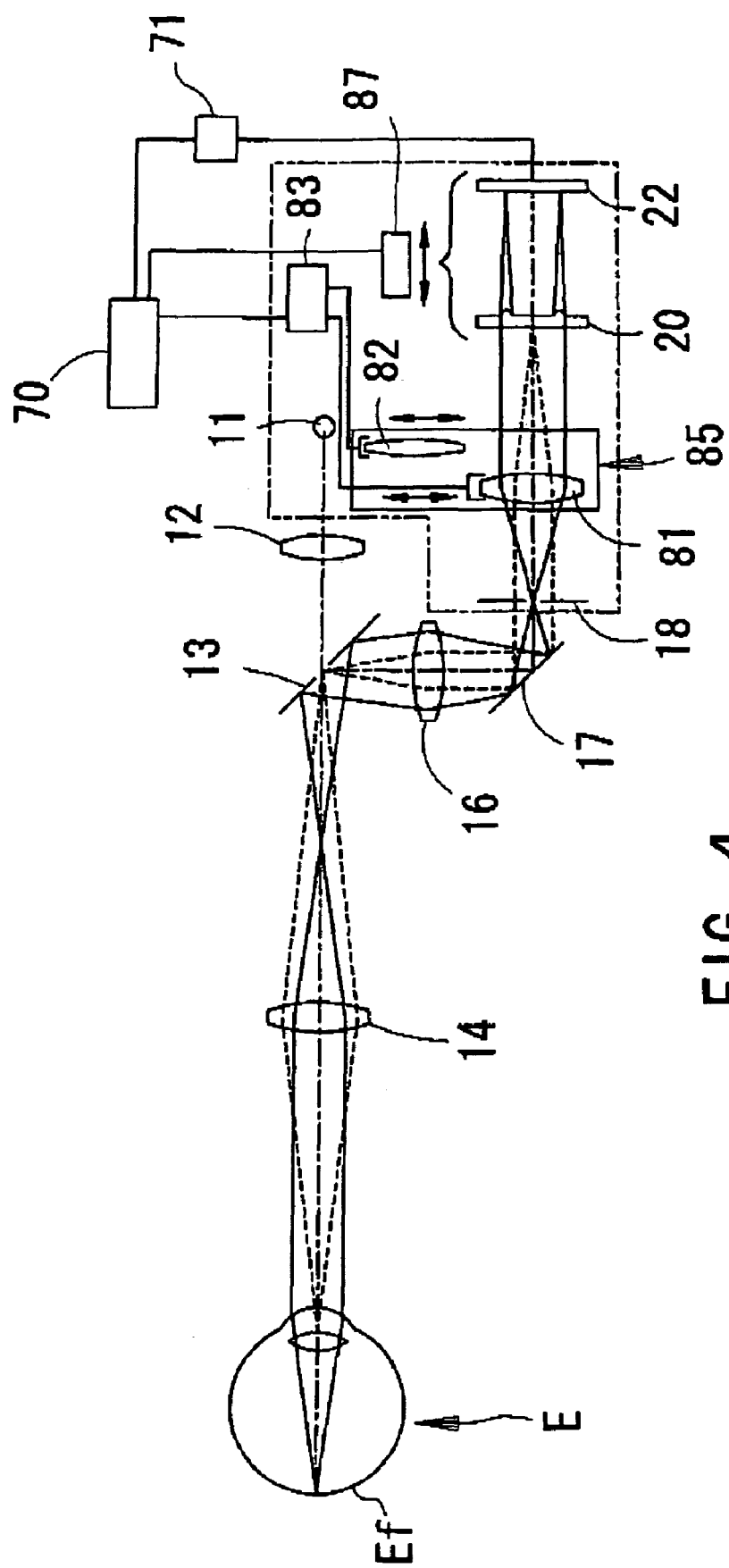
FIG. 4 is a view showing a schematic configuration of another example of the measurement optical system and the control system in the eye refractive power measurement apparatus.

FIG. 4 is a view showing a schematic configuration of another example (the second example) of the measurement optical system and the control system in the measurement apparatus. In the second example, as a means of changing the size of the ring-shaped aperture on the pupillary surface, not the ring lens 20 is switched to the ring lens 21 of a different ring size, but a variable power optical system 85 is employed to change a projecting magnification of the ring lens 20 onto the pupillary surface. The variable power optical system 85 is provided with collimator lenses 81 and 82 of different focal lengths switching is made to arrange one of the collimator lenses 81 and 82 on the optical axis L1 by a movement part 83 so as to bring the diaphragm 18 at each of their front focal points. At the same time, in order to make the ring lens 20 positioned at a rear focal point of the collimator lens 81 or 82, the ring lens 20 and the image-pickup element 22 are integrally moved in the optical axis L1 direction by a movement part 87 in accordance with the switching between the collimator lenses 81 and 82.

Figure 5:
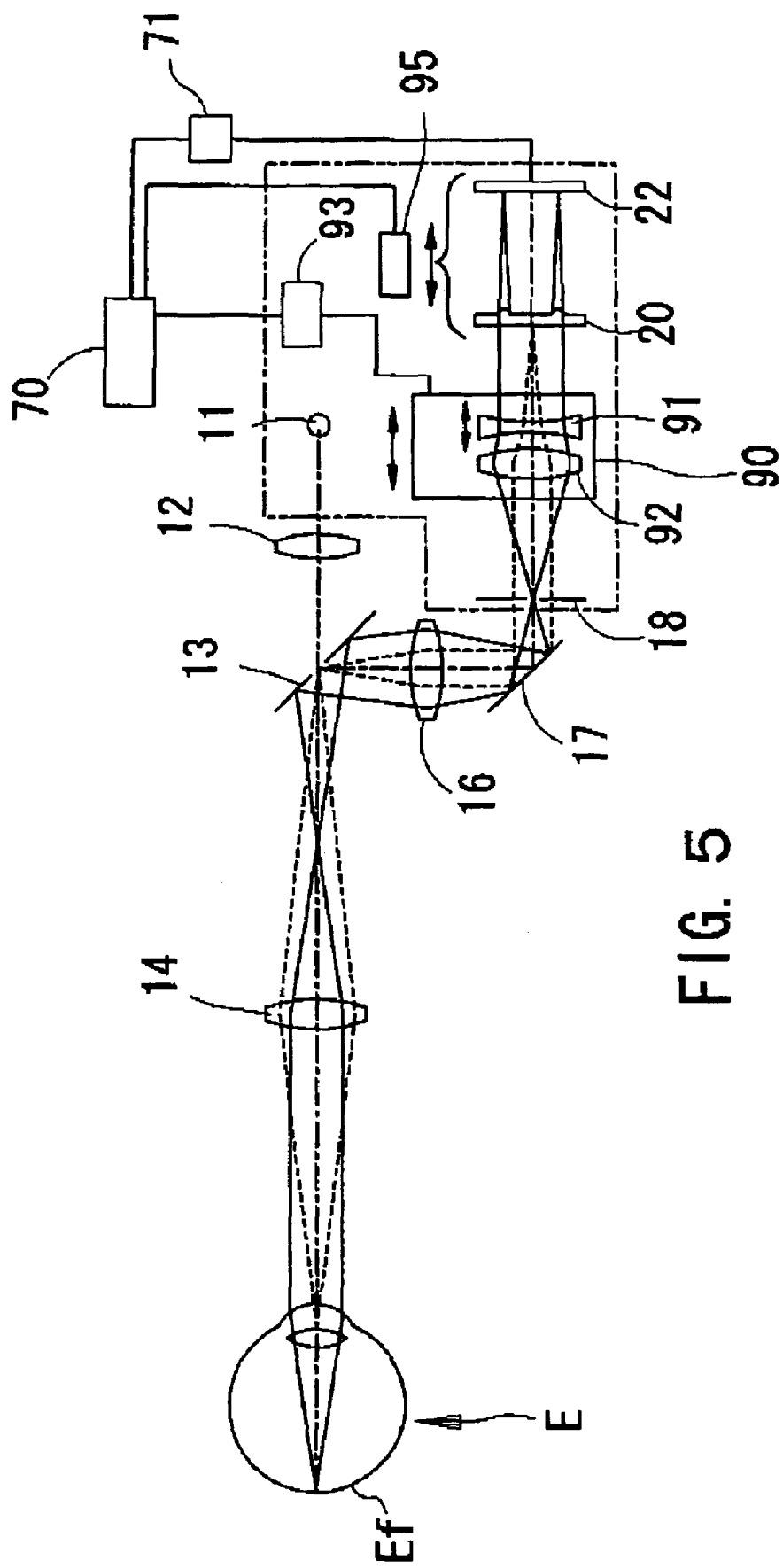
FIG. 5 is a view showing a schematic configuration of still another example of the measurement optical system and the control system in the eye refractive power measurement apparatus.

FIG. 5 is a view showing a schematic configuration of still another example (the third example) of the measurement optical system and the control system in the measurement apparatus. In the third example, a variable power optical system 90 is employed where a zooming lens is used to change successively the projecting magnification of the ring lens 20 onto the pupillary surface. The variable power optical system 90 is for example constituted of a concave lens 91 and a convex lens 92, and the concave lens 91 is moved in the optical axis L1 direction by a movement part 93 to change the total focal length of the variable power optical system 90 and change the projecting magnification of the ring lens 20 onto the pupillary surface. Also in this case, the diaphragm 18 and the ring lens 20 are arranged to be positioned at front and rear focal points of the variable power optical system 90. Therefore, the entire variable power optical system 90 is moved in the optical axis L1 direction by the movement part 93 in accordance with the set focal length, and the ring lens 20 and the image-pickup element 22 are integrally moved in the optical axis L1 direction by a movement part 95.

Figure 6:
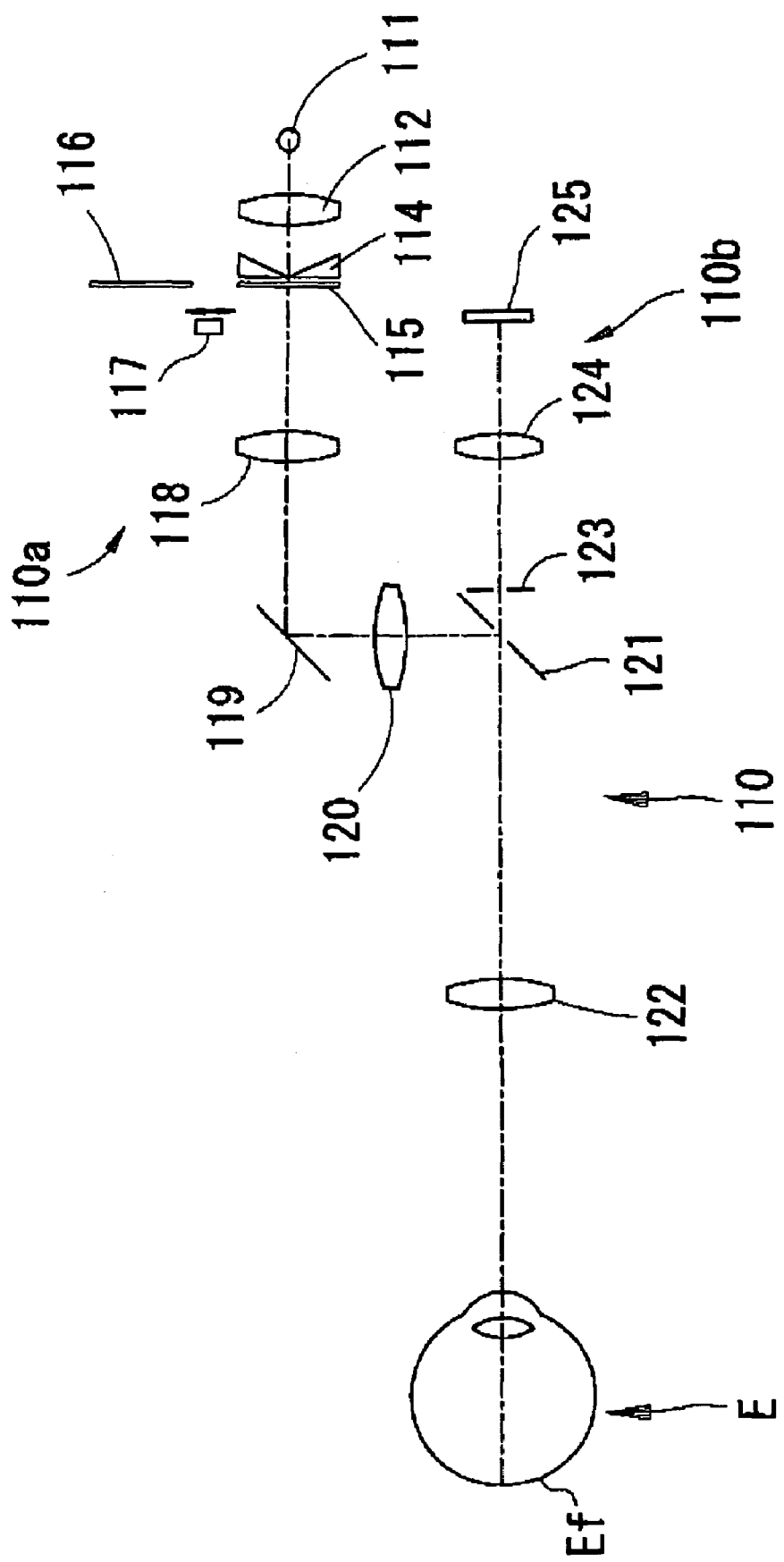
FIG. 6 is a view showing a schematic configuration of another example of the measurement optical system in the eye refractive power measurement apparatus.

FIG. 6 is a view showing a schematic configuration of another example (the fourth example) of the measurement optical system in the measurement apparatus. In the fourth example, a projection optical system 110a in a measurement optical system 110 includes an infrared light source 111, a relay lens 112, a conic prism 114, an aperture member 115 with a ring-shaped aperture (opening), a relay lens 118, a reflection mirror 119, a relay lens 120, a hole mirror 121, and an objective lens 122. The aperture member 115 is arranged to have a positional relationship optically approximately conjugate with the pupil of the eye E. In addition, the aperture member 115 and an aperture member 116 of a different ring-shaped aperture (opening) size (a ring size) are selectively switched and arranged by a movement part 117. The ring size of the aperture member 115 is for example 2.0 mm in inside diameter and 2.8 mm in outside diameter on the pupillary surface of the eye E. And, the ring size of the aperture member 116 is for example 1.4 mm in inside diameter and 2.4 mm in outside diameter on the pupillary surface.

Measurement light from the light source 111 is made parallel light by the lens 112, and passes through the prism 114, the aperture member 115 or 116, the lens 118, the mirror 119, the lens 120, the mirror 121, and the lens 122, and enters the peripheral pupillary portion so that ring-shaped light is projected onto the fundus Ef.

A photo-receiving optical system 110b shares the lens 122 and the mirror 121 in the projection optical system 110a and includes a photo-receiving diaphragm 123, a relay lens 124, and an image-pickup element 125 being a two-dimensional photodetector such as a CCD. The diaphragm 123 is arranged to have a positional relationship optically approximately conjugate with the pupil of the eye E, and the image-pickup element 125 is arranged to have a positional relationship optically approximately conjugate with the fundus Ef. The ring-shaped light from the fundus Ef passes through the central pupillary portion, the lens 122, the mirror 121, the diaphragm 123, and the lens 124 to form a ring image on the image-pickup element 125.

The ring size of the aperture member 116 is smaller than the aperture member 115; therefore, small ring-shaped light can be made enter the pupil of the eye E, and the ring-shaped light can be projected onto the fundus Ef even for the eye E with a small pupil diameter. Accordingly, by switching and arranging the aperture members 115 and 116, measurement while maintaining measurement accuracy can be performed to the normal eye with a large enough pupil diameter, and measurement can also be performed to the eye with a small pupil diameter. The switching and arrangement of the aperture members 115 and 116 may be performed in the same manner as the examples mentioned above.

Next, description will be given on a case where eye refractive power distribution of the eye E is measured. Though the description below mentions the measurement optical system of the third example shown in FIG. 5, the same measurement can be performed using the measurement optical system of the other examples.

The control part 70 judges completion of the alignment of the measurement part 4 with the eye E and automatically generates the measurement starting signal to implement pre-measurement. Then, based on the result, the eye E is fogged by the movement of the fixation target 32. In the pre-measurement, a position of the variable power optical system 90 is set so that the size of the ring-shaped aperture on the pupillary surface becomes about 3 mm in diameter. Next, the control part 70 controls the movement part 93 to move the variable power optical system 90 at a given step, and sequentially changes the projecting magnification of the ring lens 20 onto the pupillary surface and sequentially changes the size of the ring-shaped light picked up from the peripheral pupillary portion at a fixed step (for example, a range from 1.5 mm to 6.0 mm in diameter of the size of the ring-shaped aperture on the pupillary surface is set as a measurement range, and the size is changed from 1.5 mm at a step of 0.5 mm in increments of one-thirtieths of a second). In addition, the change in the size of the ring-shaped aperture is performed in synchronization with the image capture at the image-pickup element 22. In the image processing part 71, the respective ring images are separately processed. Therefore, different from a case where a plurality of the ring images are simultaneously picked up, accurate measurement can be performed even with a great local change in the refractive error.

When the ring images of which the ring size is sequentially changed as mentioned above are detected, the control part 70 calculates refractive power of each ring size in each meridian direction (for example, every 5 degrees) relative to a central position of the minimum ring. Then, the refractive power distribution on the pupillary surface is obtained by conforming the refractive values obtained for each ring size to each pupil part. The result is displayed on the monitor 7 for example as distribution in density variation or color variation. In addition, the refractive values (S, C, A) for each ring size may be displayed.

Incidentally, in the measurement of the refractive power distribution, if the pupil diameter of the eye E is detected and the maximum diameter of the ring size sequentially changed are determined previously, efficient measurement can be performed.

In addition, the control part 70 synchronizes the image capture by the image-pickup element 22 and that by the image-pickup element 52 in the observation optical system 50 at the time of the measurement of the refractive power and detects the applicability of the alignment state when the ring size is sequentially changed. As described above, the applicability of the alignment state in the X- and Y-directions is detected from the alignment target image formed by the alignment target projection optical system 40, and the applicability of the alignment state in the Z-direction is detected from the four alignment target images formed by the alignment target projection optical system 45. And, when an alignment deviation is detected in any ring image of which the ring size has been changed, the control part 70 judges not to use the ring image of that size in calculation of the refractive power distribution, and implements re-measurement in a state where the alignment is completed. The re-measurement here may be performed for only the ring size where the alignment deviation is detected. Consequently, an accurate measurement result of the refractive power distribution can be obtained.

In addition, in the aforementioned measurement of the refractive power distribution, time and trouble of the re-measurement can be saved by correcting measurement data with each ring size based on deviation information on the alignment state when the ring size is sequentially changed. For the correction of a deviation amount in the X- and Y-directions, a model eye with certain power is used to acquire a ring image which is deviated at a certain distance (for example, 1 mm) in the X-direction and obtain it s ring shape. In the case of the alignment deviation in the X- and Y-directions, as the ring shape changes to an oval shape by tilting, its shape is obtained for each direction. A length L from the center of the ring shape is obtained for each direction (for example, every 1 degree), and a correction equation $L=a\Delta x+b$ is calculated for each direction. $\Delta x$ is the deviation amount. Similarly, a ring image which is deviated at a certain distance in the Y-direction is acquired, and a correction equation $L=a\Delta y+b$ is calculated for each direction. With these equations, the actually acquired ring shape is corrected based on the respective deviation amounts $\Delta x$ and $\Delta y$ in the X- and Y-directions obtained in the alignment detection. As for the Z-direction, since the total size of the ring shape is changed in accordance with the deviation amount $\Delta z$, correction can be made by obtaining the ring size in accordance with the alignment deviation amount $\Delta z$ for each diopter. Besides, the correction method is not limited thereto, and various methods can be adopted.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus for measuring eye refractive power of an eye of an examinee, the apparatus comprising:
   an observation optical system having a first image pickup element which picks up an image of an anterior segment of the eye;
   a measurement optical system including:
      a projection optical system for projecting ring-shaped measurement light onto a fundus of the eye via a ring-shaped aperture arranged at an approximately conjugate position with a pupil of the eye, where a diameter on the pupil of the ring-shaped aperture is changed, and at least one of the diameter on the pupil of the ring-shaped aperture is such that measurement can be performed even to the eye with a small pupil diameter; and
      a photo-receiving optical system for forming a ring-shaped image on a second image pickup element by picking up the ring-shaped measurement light reflected from the fundus via a central portion of the pupil;
   changing means for changing the diameter on the pupil of the ring-shaped aperture; and
   calculation means for calculating the eye refractive power based on an image pickup result obtained by the second image pickup element.

2. The eye refractive power measurement apparatus according to claim 1, further comprising pupil detecting means for detecting at least one of a diameter and a position of the pupil based on the presence or absence of at least one of a crack and insufficient intensity in the ring-shaped image picked up by the second image pickup element,
   wherein the changing means changes the diameter on the pupil of the ring-shaped aperture based on a detection result obtained by the pupil detecting means.

3. The eye refractive power measurement apparatus according to claim 1, further comprising pupil detecting means for detecting at least one of a diameter and a position of the pupil based on the anterior-segment image picked up by the first image pickup means,
   wherein the changing means changes the diameter on the pupil of the ring-shaped aperture based on a detection result obtained by the pupil detecting means.

4. An eye refractive power measurement apparatus for measuring eye refractive power of an eye of an examinee, the apparatus comprising:
   an observation optical system having a first image pickup element which picks up an image of an anterior segment of the eye;
   a measurement optical system including:
      a projection optical system for projecting spot-shaped measurement light onto a fundus of the eye via a central portion of a pupil of the eye; and
      a photo-receiving optical system for forming a ring-shaped image on a second image pickup element by the spot-shaped measurement light reflected from the fundus via an aperture member including a ring-shaped aperture by one of selectively arranging a plurality of the aperture members of which the ring-shaped apertures are different in diameter at an approximately conjugate position with the pupil, and arranging the aperture member including the ring-shaped aperture at the approximately conjugate position with the pupil and arranging a variable power optical system on an eye side of the aperature member;
   changing means for changing a diameter on the pupil of the ring-shaped aperture by one of selectively arranging the aperture member and changing magnification of the ring-shaped image by the variable power optical system, where at least one of the diameter on the pupil of the ring-shaped aperture is such that measurement can be performed even to the eye with a small pupil diameter; and
   calculation means for calculating the eye refractive power based on an image pickup result obtained by the second image pickup element.

5. The eye refractive power measurement apparatus according to claim 4, further comprising pupil detecting means for detecting at least one of a diameter and a position of the pupil based on the presence or absence of at least one of a crack and insufficient intensity in the ring-shaped image picked up by the second image pickup element,
   wherein the changing means changes the diameter on the pupil of the ring-shaped aperture based on a detection result obtained by the pupil detecting means.

6. The eye refractive power measurement apparatus according to claim 4, further comprising pupil detecting means for detecting at least one of a diameter and a position of the pupil based on the anterior-segment image picked up by the first image pickup means,
   wherein the changing means changes the diameter on the pupil of the ring-shaped aperture based on a detection result obtained by the pupil detecting means.

7. An eye refractive power measurement apparatus for measuring eye refractive power of an eye of an examinee, the apparatus comprising:
   an observation optical system having a first image pickup element which picks up an image of an anterior segment of the eye;
   a measurement optical system including:
      a projection optical system for projecting measurement light onto a fundus of the eye via a ring-shaped aperture arranged at an approximately conjugate position with a pupil of the eye, where a diameter on the pupil of the ring-shaped aperture is changed; and
      a photo-receiving optical system for forming a ring-shaped image on a second image pickup element by picking up the ring-shaped measurement light reflected from the fundus via a central portion of the pupil;
   changing means for changing the diameter on the pupil of the ring-shaped aperture at a given step from the center to the periphery of the pupil in response to a measurement starting signal; and
   calculation means for calculating distribution of the eye refractive power based on an image pickup result obtained by the second image pickup element.

8. An eye refractive power measurement apparatus for measuring eye refractive power of an eye of an examinee, the apparatus comprising:

an observation optical system having a first image pickup element which picks up an image of an anterior segment of the eye;

a measurement optical system including:
- a projection optical system for projecting spot-shaped measurement light onto a fundus of the eye via a central portion of a pupil of the eye; and
- a photo-receiving optical system for forming a ring-shaped image on a second image pickup element by the spot-shaped measurement light reflected from the fundus via an aperture member including a ring-shaped aperture by one of selectively arranging a plurality of the aperture members of which the ring-shaped apertures are different in diameter at an approximately conjugate position with the pupil, and arranging the aperture member including the ring-shaped aperture at the approximately conjugate position with the pupil and arranging a variable power optical system on an eye side of the aperture member;

changing means for changing a diameter on the pupil of the ring-shaped aperture by one of selectively arranging the aperture member and changing magnification of the ring-shaped image by the variable power optical system at a given step from the center to the periphery of the pupil in response to a measurement starting signal; and calculation means for calculating distribution of the eye refractive power based on an image pickup result obtained by the second image pickup element.

* * * * *